(12) United States Patent
McRury et al.

(10) Patent No.: US 7,115,100 B2
(45) Date of Patent: Oct. 3, 2006

(54) TISSUE BIOPSY AND PROCESSING DEVICE

(75) Inventors: Ian D. McRury, Medway, MA (US); Francois Binette, Weymouth, MA (US); Julia Hwang, Watertown, MA (US)

(73) Assignee: Ethicon, Inc., Somerville, NJ (US)

( * ) Notice: Subject to any disclaimer, the term of this patent is extended or adjusted under 35 U.S.C. 154(b) by 253 days.

(21) Appl. No.: 10/298,091

(22) Filed: Nov. 15, 2002

(65) Prior Publication Data
US 2004/0097829 A1   May 20, 2004

(51) Int. Cl.
*A61B 10/00* (2006.01)

(52) U.S. Cl. ............... 600/562; 600/563; 600/564

(58) Field of Classification Search ........ 600/562–567; 606/167
See application file for complete search history.

(56) References Cited

U.S. PATENT DOCUMENTS

| | | | |
|---|---|---|---|
| 5,197,483 A * | 3/1993 | Rogalsky et al. ........... 600/562 |
| 5,398,690 A | 3/1995 | Batten et al. |
| 5,827,305 A | 10/1998 | Gordon |
| 5,871,462 A | 2/1999 | Yoder et al. |
| 5,913,859 A | 6/1999 | Shapira |
| 5,944,686 A | 8/1999 | Patterson et al. |
| 6,022,354 A | 2/2000 | Mercuri et al. |
| 6,071,284 A | 6/2000 | Fox |
| 6,216,573 B1 | 4/2001 | Moutafis et al. |
| 6,280,398 B1 | 8/2001 | Ritchart et al. |
| 6,375,635 B1 | 4/2002 | Moutafis et al. |
| 6,451,017 B1 | 9/2002 | Moutafis et al. |
| 6,485,436 B1 * | 11/2002 | Truckai et al. ............. 600/564 |
| 6,572,578 B1 * | 6/2003 | Blanchard ................... 604/22 |
| 6,736,799 B1 * | 5/2004 | Erbe et al. .................. 604/181 |
| 2001/0043918 A1 * | 11/2001 | Masini et al. ............. 424/93.7 |
| 2002/0029055 A1 | 3/2002 | Bonutti |
| 2002/0082631 A1 | 6/2002 | Bonutti |
| 2002/0091403 A1 | 7/2002 | Bonutti |
| 2002/0091406 A1 | 7/2002 | Bonutti |
| 2002/0099401 A1 | 7/2002 | Bonutti |
| 2003/0114936 A1 * | 6/2003 | Sherwood et al. ........ 623/23.58 |
| 2004/0142861 A1 * | 7/2004 | Mansbridge ................ 514/12 |

FOREIGN PATENT DOCUMENTS

| EP | 13 89 548 | 2/2004 |
|---|---|---|
| WO | WO 02/089722 | 11/2002 |

* cited by examiner

*Primary Examiner*—Max F. Hindenburg
*Assistant Examiner*—Jonathan Foreman
(74) *Attorney, Agent, or Firm*—Nutter, McClennen & Fish LLP

(57) ABSTRACT

A tissue biopsy and processing device for capturing and processing a tissue sample is provided. In general, the device includes a biopsy member adapted to remove a tissue sample from a patient's body, and a processing apparatus adapted to receive the tissue sample from the biopsy device, and to dissociate and mince the tissue sample in preparation for further use. The processing apparatus can include a tissue reducing chamber in communication with and adapted to receive the tissue sample from the biopsy member, and a tissue processing element associated with the tissue reducing chamber that is effective to dissociate the tissue sample retained within the tissue reducing chamber.

19 Claims, 7 Drawing Sheets

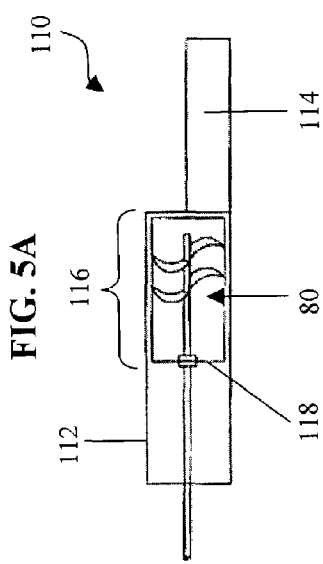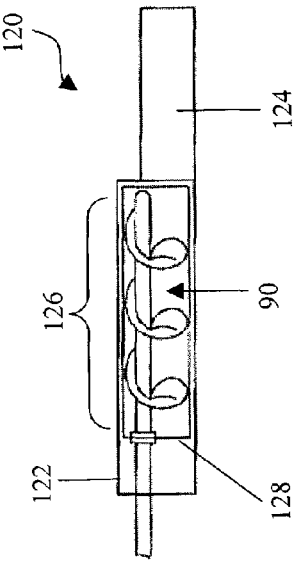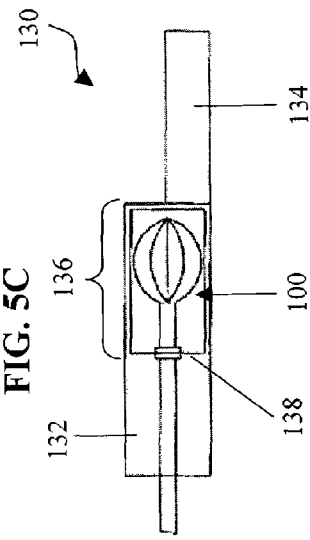

TISSUE BIOPSY AND PROCESSING DEVICE

FIELD OF THE INVENTION

The present invention relates generally to tissue biopsy and processing devices.

BACKGROUND OF THE INVENTION

Bone grafts are often used to treat fractures, gaps in bones caused by trauma or infection, revision joint surgery, and oral/maxillofacial surgery. Bone grafts provide a framework into which the host bone can regenerate and heal. Once implanted, the bone cells weave into and through the porous microstructure of the bone graft to support the new tissue, blood cells and soft tissue as they grow to connect fractured bone segments.

The loss or failure of tissue is one of the most frequent and costly problems in human health care. In recent years, grafting has evolved from the initial autograft and allograft preparations to biosynthetic and tissue-engineered living replacements. Tissue engineering enables the growth of transplantable functional tissue replacements starting from samples of autologous cells of the patient. The cells are obtained by harvesting tissue from a patient using a biopsy and then cells are extracted from the tissue sample and cultured to the appropriate numbers in the laboratory. These living cells are then placed in a three-dimensional natural or synthetic scaffold or matrix, and are kept under tissue specific culture conditions to ensure differentiation and tissue maturation. If provided with the appropriate conditions and signals, the cells will secrete various matrix materials to create an actual living tissue that can be used as a replacement tissue to be implanted back into the defective site in the patient.

Current tissue engineering procedures involve a multi-step process. First, a biopsy is performed to remove a tissue sample from a patient's body. A variety of biopsy devices are well known in the art. U.S. Pat. No. 6,375,635 of Moutafis et al., for example, discloses a biopsy device that employs a high-pressure fluid jet that is effective to cut and retrieve a tissue sample. Once the biopsy procedure is complete, the tissue sample is then sent to a laboratory, where the tissue is prepared for cell isolation. The isolated cells can then be placed into a three-dimensional scaffold for subsequent growth and eventually implantation back into the patient.

While current procedures have proven effective, they can be very time-consuming and costly. Accordingly, there exists a need for more efficient and effective methods and devices for obtaining and processing a tissue sample.

SUMMARY OF THE INVENTION

The present invention provides a tissue biopsy and processing device for capturing and processing a tissue sample. In general, the device includes a biopsy member adapted to remove a tissue sample from a patient's body, and a processing apparatus adapted to receive the tissue sample from the biopsy device, and to dissociate and mince the tissue sample in preparation for further use. The processing member can include a tissue reducing chamber in communication with and adapted to receive the tissue sample from the biopsy member, and a tissue processing element associated with the tissue reducing chamber and effective to dissociate the tissue sample retained within or moving through the tissue reducing chamber.

In one embodiment, the device can be an elongate member having a proximal end, a distal end, and an inner lumen extending therebetween. The biopsy member is preferably formed on the distal end of the elongate member, and is effective to retrieve and convey a tissue sample to the tissue reducing chamber. A variety of biopsy members can be used with the present invention. By way of non-limiting example, the biopsy member can be a suction member, a cutting member, a burr, a shaver, a curette, a rongeur, a high pressure fluid jet, a grasping member, a needle, and combinations thereof. The tissue reducing chamber is preferably formed within the inner lumen of the elongate member just proximal to the distal end, and can be formed integrally with the biopsy member.

In another embodiment, the tissue reducing chamber can include an isolation member effective to prevent foreign substances from entering the reducing chamber after a tissue sample is disposed within the chamber. The isolation member can be, for example, a hinged flap movable between an open position, in which the chamber can receive a tissue sample, and a closed position, in which the chamber is sealed. The tissue processing element is preferably disposed within the tissue reducing chamber, and can comprise a high pressure fluid jet. Alternatively, the tissue processing element can comprise a mechanical cutting element. The mechanical cutting element can be, for example, an auger, a rongeur, a curette, an awl, a reamer, a corer, a blade, a grinding member, a grating member, and combinations thereof.

The device can also optionally include a tissue retaining element for holding a tissue sample in the reducing chamber. The tissue retaining element can also assist in enabling the high pressure fluid jet to apply a high pressure fluid to the tissue to process the tissue. The tissue retaining element can comprise a filter having pores sufficient to retain the tissue, while allowing the high pressure fluid to flow therethrough. In another embodiment, the device can include a siphoning member in communication with the tissue reducing chamber that is effective to receive a tissue sample, after the tissue sample is processed by the tissue processing element, and to remove excess fluid from the tissue sample. The device can also optionally include a bioimplantable tissue scaffold in communication with the tissue reducing chamber that is effective to receive a tissue sample after the tissue sample is processed by the tissue processing element.

The present invention also provides methods for preparing a tissue slurry. In one embodiment, the method includes the step of providing a device having a biopsy member for retrieving a tissue sample from a patient, and a processing element in communication with the biopsy member that is effective to dissociate and mince the tissue sample. The method further includes the steps of removing a tissue sample from a patient's body using the biopsy member, and processing the tissue sample with the processing element to dissociate and mince the tissue. The method can further include the step of collecting the dissociated and minced tissue for subsequent use.

BRIEF DESCRIPTION OF THE DRAWINGS

The invention will be more fully understood from the following detailed description taken in conjunction with the accompanying drawings, in which like reference numerals designate like parts throughout the various figures, and wherein:

FIGS. 5A–5C are side view illustrations of various embodiments of a tissue biopsy and processing device;

DETAILED DESCRIPTION OF THE INVENTION

Figure 1A:
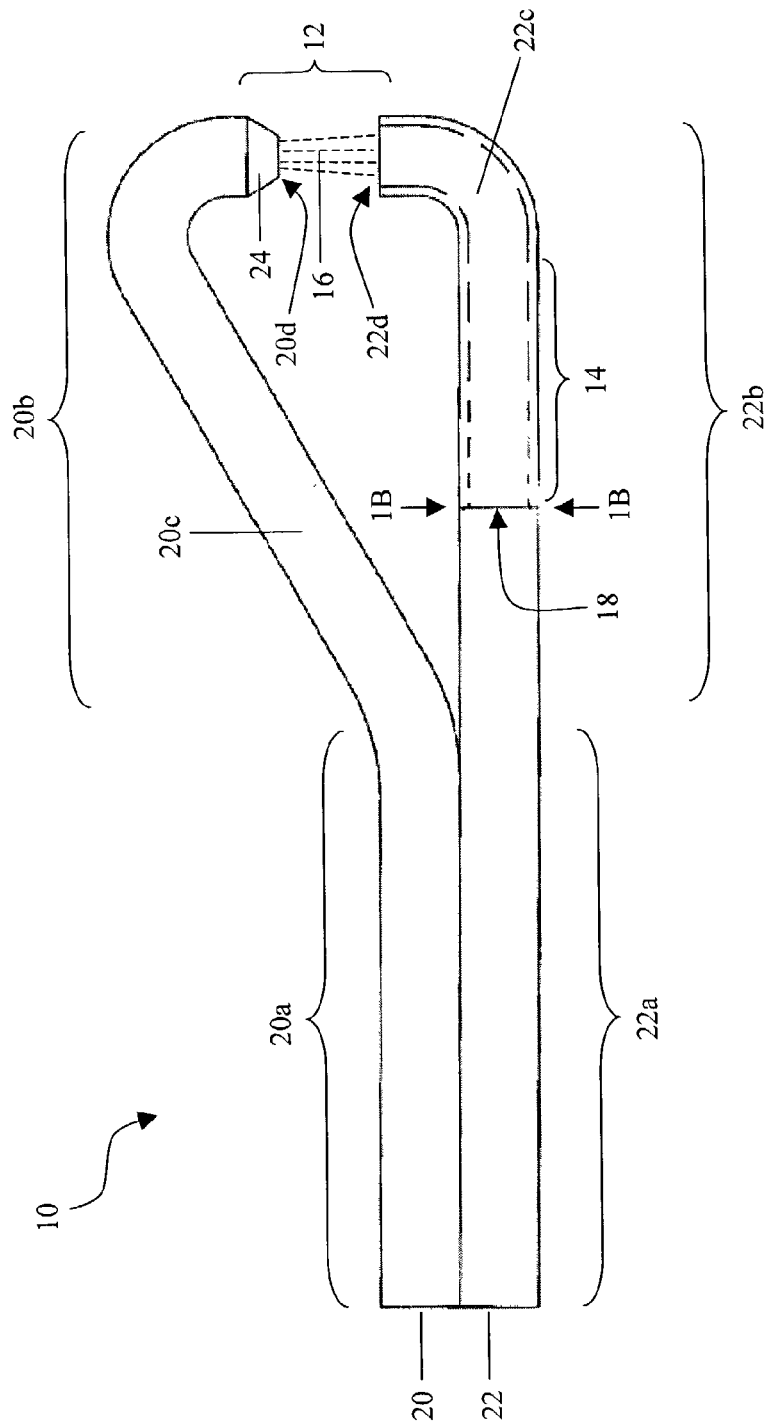
FIG. 1A is a side view illustration of a tissue biopsy and processing device according to one embodiment of the present invention.

The present invention provides a tissue biopsy and processing device that is effective to capture and prepare a tissue sample. FIG. 1 illustrates one embodiment of a tissue biopsy and processing device 10. As shown, the device 10 generally includes a biopsy member 12 that is adapted to remove a tissue sample from a patient's body, and a tissue processing apparatus having a tissue reducing chamber 14 that is in communication with and is adapted to receive the tissue sample from the biopsy member 12, and a tissue processing element 16 associated with the tissue reducing chamber 14 and that is effective to dissociate the tissue sample retained within the reducing chamber 14. The device 10 further includes a tissue retaining element 18 for holding the tissue sample in the reducing chamber while the tissue processing element 16 dissociates the tissue. The device is particularly advantageous in that it allows the biopsy and tissue preparation to be completed in one step, thereby saving time and reducing costs.

The device 10 can have a variety of configurations. As shown in FIG. 1, the device has a generally elongate shape and includes first and second hollow elongate members, e.g., tubes 20, 22. The first and second tubes 20, 22 each include a proximal portion 20a, 22a, a distal portion 20b, 22b, and an inner lumen 20c, 22c extending therebetween. The distal portion 20b, 22b of each tube 20, 22 is spaced a distance apart from one another, and each tube 20, 22 includes a distal-most end 20d, 22d with openings in facing relationship with one another. The proximal end (not shown) of the first tube 20 is in fluid communication with a high-pressure fluid source that is effective to direct fluid at a high pressure through the first tube 20 and out the distal-most end 20d of the tube 20 toward the distal-most end 22d of the second tube 22. The distal-most end 20d of the first tube 20 can optionally include a nozzle 24 for controlling the direction of fluid flow toward the second tube 22. In use, the high pressure fluid source forms the tissue biopsy member 12, as the fluid is effective to cut through and remove a tissue sample from a patient's body. The device 10 is used by placing the device 10 at a site in a patient's body and positioning the desired tissue sample between the distal-most end 20d, 22d of each tube 20, 22. The fluid source is then activated to cause the high pressure fluid flow to cut through the tissue to remove a tissue sample, directing it to lumen 22c.

Figure 1B:
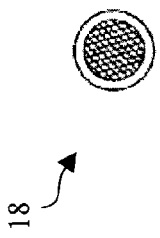
FIG. 1B is a cross-section view of the device of FIG. 1A taken across line 1B—1B.

Once the tissue sample is retrieved, the sample and the fluid flow into the second tube 22, which includes a tissue reducing chamber 14 that is effective to receive the high pressure fluid flow and the tissue sample from the first tube 20. The reducing chamber 14 can have any shape and size, and can merely be a portion of the inner lumen 22c positioned just proximal to the distal-most end 22d of the second tube 22. The reducing chamber 14 can optionally include a tissue retaining element 18 that is effective to retain the tissue sample in the reducing chamber 14. The retaining element 18 can have a variety of configurations, and can be, for example, a screen-like member, as shown in FIG. 1B.

Preferably, the tissue retaining element 18 includes pores having a diameter sufficient to allow fluid to flow therethrough, but to prevent tissue having a particular size from passing therethrough. In use, the retaining element 18 will retain the tissue sample while the high pressure fluid 16 flows therethrough. In this respect, the high pressure fluid 16 serves as the processing element in that it is effective to dissociate, mince, or otherwise chop the tissue into small particles. Once the tissue sample is dissociated, the tissue particles preferably have a diameter sized to pass through the retaining element 18, where the tissue particles are collected for further use. In an exemplary embodiment, the particle size of each tissue fragment can vary, for example, the tissue size can be in the range of about 0.1 and 3 mm$^3$, in the range of about 0.5 and 1 mm$^3$, in the range of about 1 to 2 mm$^3$, or in the range of about 2 to 3 mm$^3$, but preferably the tissue particle is less than 1 mm$^3$.

In an alternate embodiment, the tissue retaining element 18 can serve as a siphoning member that is effective to receive the dissociated tissue sample and to separate the sample from the fluid. In this respect, the siphoning member has pores having a diameter less than a diameter of the dissociated tissue, thereby preventing the dissociated tissue to pass therethrough and collecting the tissue as it is being processed. The siphoning member can optionally be, for example, a biological implant, such as a tissue scaffold, for receiving the dissociated tissue and thereby preparing the scaffold for subsequent implantation.

Figure 2:
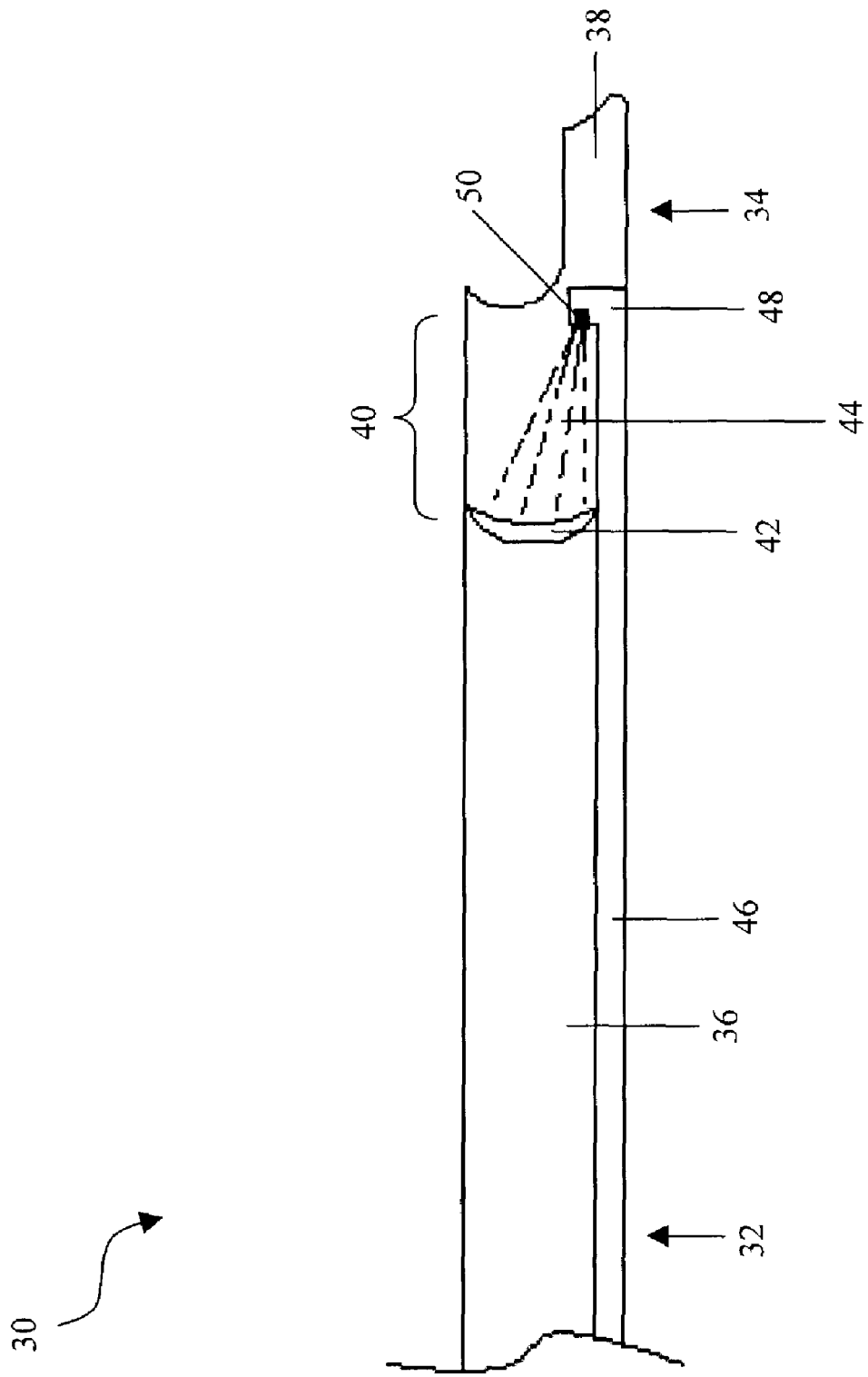
FIG. 2 is a side view illustration of another embodiment of a tissue biopsy and processing device according to the present invention.

FIG. 2 illustrates another embodiment of a tissue biopsy and processing device 30. As shown, the device 30 has a generally elongate shape and includes a proximal end 32, a distal end 34, and an inner lumen 36 extending therebetween. A biopsy member 38 is formed on the distal end 34 of the device 30, and a reducing chamber 40 is formed in a distal portion of the device 30 at a location proximal to the biopsy member 38. The reducing chamber 40 includes a tissue retaining member 42 that is effective to retain the tissue sample in the chamber 40, and a tissue processing element 44 effective to dissociate the tissue.

The biopsy member 38 can have a variety of configurations, but is preferably in the shape of an awl that is effective to cut and/or scrape a tissue sample from a patient's body. Once the sample is retrieved from the patient, the sample can either be pushed or pulled into the tissue reducing chamber 40 using a variety of techniques. By way of non-limiting example, a fluid flow can be used to push the sample into the reducing chamber 40, or alternatively a vacuum can be coupled to the proximal end 32 of the device 30 to pull the tissue sample into the reducing chamber 40. Once the tissue sample is disposed in the reducing chamber 40, the retaining member 42. e.g., a screen similar to screen 18 shown in FIG. 1, will retain the tissue sample in the reducing chamber 40.

The processing element 44 can then be used to dissociate the minced tissue. As shown in FIG. 2. the processing element 44 is formed from a high pressure fluid flow directed toward the tissue retaining member 42 and that is effective to dissociate, chop, and/or mince the tissue into small particles. The fluid is preferably directed through an elongate tube or channel 46 formed in the inner lumen 36 of the device 30. The elongate tube or channel 46 includes a proximal end (not shown) in communication with a fluid source, and a distal end 48 having a nozzle 50 or similar member formed thereon. The nozzle 50 is positioned in the reducing chamber 40 adjacent the distal end 34 of the device 30, and is in facing relationship with the tissue retaining element 42. The nozzle 50 is effective to control the direction of fluid flow. Once the tissue sample is dissociated, the tissue particles can be collected on the retaining member 42, e.g., siphoning member, or can pass through the tissue retaining member 42 where they can be collected for further use.

The high pressure fluid jet used in the tissue biopsy and processing devices shown in FIGS. 1 and 2 can have a variety of configurations. Preferably, the proximal end of the shaft 20, or channel 46, is connected to a high pressure pump or liquid dispenser. The pressure and/or flow rate of the fluid jet is preferably controllable to allow the pressure and/or flow rate to be adjusted based on the type of tissue desired to be cut. Typical surgical devices are operated at a liquid pressure between about 500 psig and about 50,000 psig, depending on the intended use. Preferably, the devices of the present invention are operated at a liquid pressure in the range of about 7,000 psi and 18,000 psi. A variety of liquids can also be utilized with a tissue biopsy and processing device according to the present invention. The fluid should be capable of being maintained in a liquid state at the pressures and temperatures contemplated for performing the procedure, and should be physiologically compatible. The fluid, as well as the fluid pressure, should also be compatible with maintaining the viability of the cells within the minced tissue. Suitable fluids include, for example, saline and water. The liquid can also optionally include solid abrasives to improve cutting. Alternatively, the liquid can be a liquefied gas, such as carbon dioxide, that forms solid particulate material upon being emitted from the nozzle. The liquid can also optionally include medicaments. A person having ordinary skill in the art will appreciate that virtually any high pressure fluid device and fluid can be used with the tissue biopsy and processing device of the present invention, and that the device can be adapted based on the high pressure fluid jet desired to be used.

While FIGS. 1 and 2 illustrate two embodiments of a tissue biopsy and processing device 10, 30, a person having ordinary skill in the art will appreciate that the device can have a variety of configurations. For example, FIGS. 1 and 2 each illustrate devices 10, 20 that utilize a high pressure fluid jet to dissociate tissue. However, a variety of dissociating members can be used in place of, or in addition to, the high pressure fluid jet. Suitable dissociating members include, for example, mechanical cutting elements, such as augers, rongeurs, curettes, awls, reamers, corers, blades, grinding members, grating members, and combinations thereof. A tissue biopsy and processing device according to the present invention can also include a variety of biopsy devices. Suitable biopsy devices include, for example, a suction member, a cutting member, a burr, a shaver, a curette, a rongeur, a high pressure fluid jet, a grasping member, a needle, and combinations thereof, needles, and combinations thereof. By way of non-limiting example, FIGS. 3–5C illustrate various tissue biopsy and/or processing elements for use with a device according to the present invention.

Figure 3A:
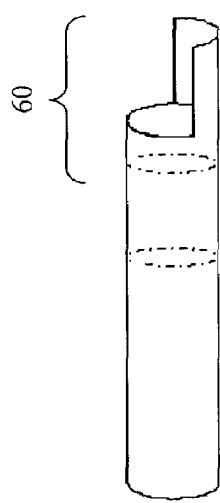
FIGS. 3A–3C illustrate embodiments of a biopsy member for use with a tissue biopsy and processing device.
Figure 3B:
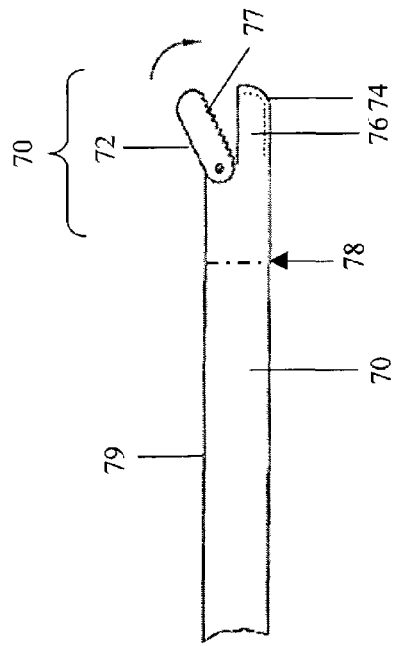
Figure 3C:
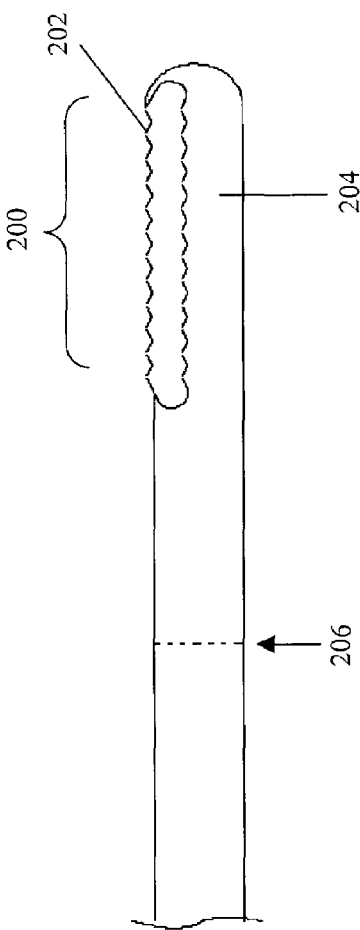

FIGS. 3A–3C illustrate alternative embodiments of a tissue biopsy member 60, 70, 200. As shown in FIG. 3A, the biopsy member 60 is in the from of an awl, similar to awl 38 shown in FIG. 2. The awl 60 is effective to scrape and/or cut tissue from a patient's body. A person having ordinary skill in the art will appreciate that the awl 60 can have virtually any shape and size, as long as it is effective to remove a tissue sample from a patient. FIG. 3B illustrates a tissue biopsy member 70 in the form of a biter. As shown, the biter 70 includes an elongate member 79 having first and second jaw members 72, 74 formed on a distal end thereof. One or both of the jaw members 72, 74 can be pivotally movable, and can include tissue penetrating teeth 77 formed thereon. As shown in FIG. 3B, the first jaw member 72 is pivotally connected to the second jaw member 74, and includes several tissue penetrating teeth 77 formed thereon and adapted to penetrate into and remove a tissue sample from a patient's body. The second jaw member 74 is integrally formed with the elongate member 79, and includes a tissue receiving recess 76 formed therein and in communication with the tissue reducing chamber 78. A trigger or similar actuation member (not shown) can be provided for moving one or both of the jaw members 72, 74 between an open position (as shown), and a closed position. FIG. 3C illustrates a biopsy member 200 in the form of a shaver having jagged edges or blades 202 which are effective to shave off a desired portion of tissue. The shaver 200 preferably includes a tissue receiving recess 204 formed therein and in communication with the tissue reducing chamber 206.

Figure 4A:
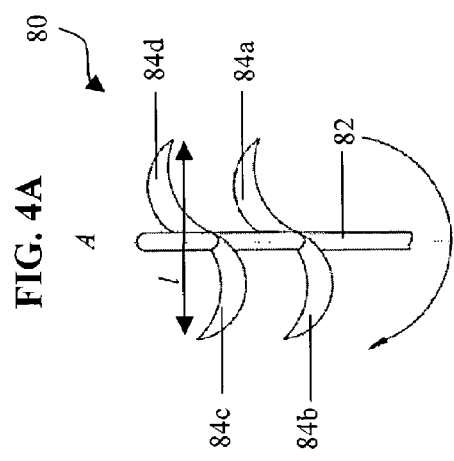
FIGS. 4A–4C illustrate embodiments of a tissue processing element for use with a tissue biopsy and processing device.
Figure 4B:
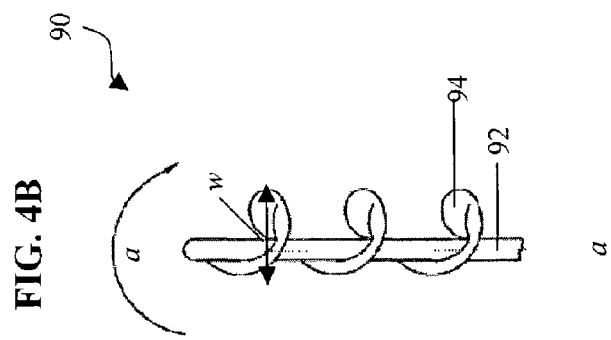
Figure 4C:
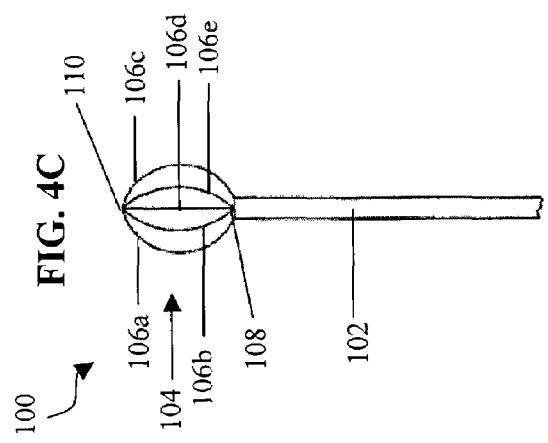

FIGS. 4A–4C illustrate alternative embodiments of a tissue processing element 80, 90, 100 which are preferably adapted to be disposed within the tissue reducing chamber of a device in accordance with the present invention. The tissue processing elements 80, 90, 100 are rotatably disposed within the reducing chamber, and are optionally slidably movable along a length of the reducing chamber. In use, the processing element 80, 90, 100, when rotated at high speeds, is effective to dissociate tissue into small particles. Rotation of the processing elements 80, 90, 100 can be accomplished using a variety of techniques, including both mechanical and/or electrical techniques.

Referring to FIG. 4A, the processing element 80 has an elongate rigid member 82 including several blade members 84a, 84b, 84c, 84d disposed on a distal portion thereof. The blade members 84a, 84b, 84c, 84d can be positioned at any location along a length of the elongate member 82, and preferably each blade member 84a, 84b, 84c, 84d extends from the elongate member 82 in a direction perpendicular to an axis A of the elongate member 82. As shown in FIG. 4A, the elongate member 82 includes a first pair of blade members 84a, 84b positioned on opposed sides of the elongate member 82, and a second pair of blade members 84c, 84d positioned on opposed sides of the elongate member 82 and spaced a distance apart from the first pair of blades 84a, 84b. Each blade member 84a, 84b, 84c, 84d can have virtually any shape and size, but preferably each blade member 84a, 84b, 84c, 84d is substantially C-shaped. Each pair of blade members 84a, 84b, 84c, 84d preferably has a combined length l that extends across the reducing chamber, such that in use the tissue sample cannot pass through the reducing chamber without coming into contact with the rotating tissue processing element 80.

FIG. 4B illustrates another embodiment of a tissue processing element 90 formed from an elongate member 92 having a single, auger-type blade member 94 rotatably disposed around an axis a of the elongate member 92 and extending along a length of the elongate member 92. The blade member 94 can have any shape and size, but preferably has a width w that, when disposed within the reducing chamber, is sufficient to occupy a significant portion of the reducing chamber to prevent the tissue sample from passing through the reducing chamber without coming into contact with the blade member 94.

FIG. 4C illustrates yet another embodiment of a tissue processing element 100 formed from a rigid elongate member 102 having a burr or grinder-type blade member 104 disposed on a distal end thereof. The blade member 104 includes several convexly shaped blades 106a–e, preferably in the form of a wire or elongate strip, that extend from a distal tip 108 of the elongate member 102 to a position 110 proximal to the distal tip 108 of the elongate member 102. Each blade 106a–e combined forms a substantially spherical shaped blade member 104.

FIGS. 5A–5C illustrate each tissue processing element 80, 90, 100 shown in FIGS. 4A–4C disposed within a tissue biopsy and processing device 110, 120, 130. As shown, each device 110, 120, 130 includes an elongate shaft 112, 122, 132 having an awl-type biopsy member 114, 124, 134, similar to awl 38 shown in FIG. 2, formed on a distal end thereof, and having a reducing chamber 116, 126, 136 disposed therein. The processing element 80, 90, 100 is disposed within the shaft 112, 122, 132 of the device 110, 120, 130 and the blade member 84, 94, 104 of each processing element 80, 90, 100 is positioned within the reducing chamber 116, 126, 136. The processing elements 80, 90, 100 can each be slidably movable along a length of the reducing chamber 116, 126, 136 to more effectively dissociate tissue disposed therein. Each tissue biopsy and processing device 110, 120, 130 can also include a tissue retaining member 118, 128, 138 disposed at a proximal end of the reducing chamber 116, 126, 136 to prevent tissue having a particular diameter from passing therethrough. Once the tissue is dissociated, e.g., chopped and/or minced into tissue particles, by the processing element 80, 90, 100, the tissue particles can be collected on the retaining member 118, 128, 138, e.g., the siphoning member, or can pass through the retaining member 118, 128, 138 for collection or further use.

In another embodiment of the invention, the tissue biopsy and processing device can optionally include a biological implant, such as a tissue scaffold, for receiving the dissociated tissue and thereby preparing the scaffold for subsequent implantation. The biological implant can be removably disposed within the tissue biopsy and processing device at a position just proximal to the retaining element, or adjacent to the retaining element. Alternatively, as previously stated, the retaining element can be a biological implant, in which case the implant acts as a siphoning member that is effective to retain the dissociated tissue and separate the tissue from the fluid. A person having ordinary skill in the art will appreciate that a variety of modifications can be made to the device to enable a biological implant to be removably disposed therein to receive the dissociated tissue sample once processing is complete.

Figure 6A:
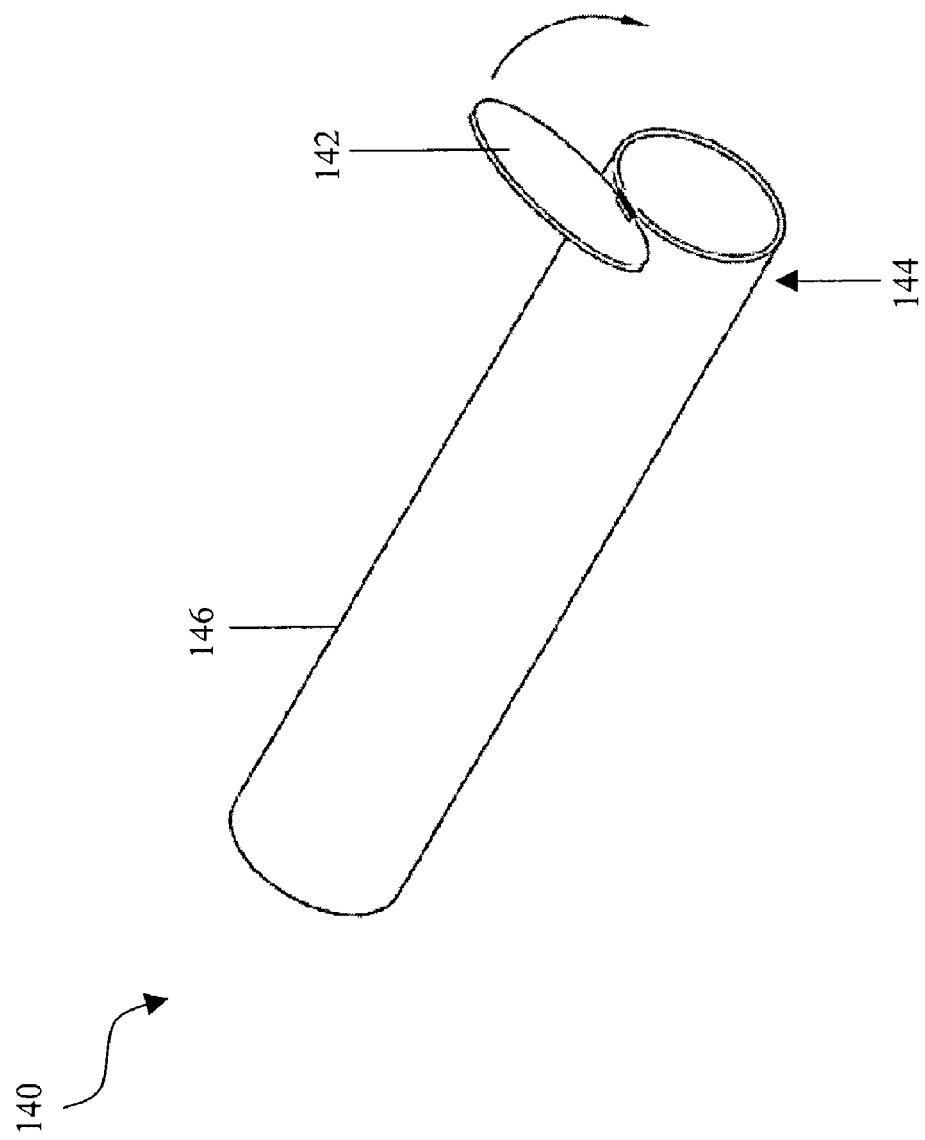
FIG. 6A is a perspective view of an isolation device for use with a tissue biopsy and processing device according to another embodiment of the present invention.

In other aspects of the invention, the tissue biopsy and processing device can optionally include an isolation member 140 effective to prevent foreign substances from entering the reducing chamber after the tissue sample is retrieved from the patient and disposed within the chamber. The isolation member 140 can have a variety of configurations, and as shown in FIG. 6 is in the form of a hinged flap 142 disposed on the distal end 144 of an elongate shaft 146. The hinged flap 142 is preferably movable between an open position (as shown), in which the tissue sample can be removed from the patient and disposed within the chamber, and a closed position (not shown), in which the chamber is sealed.

Figure 6B:
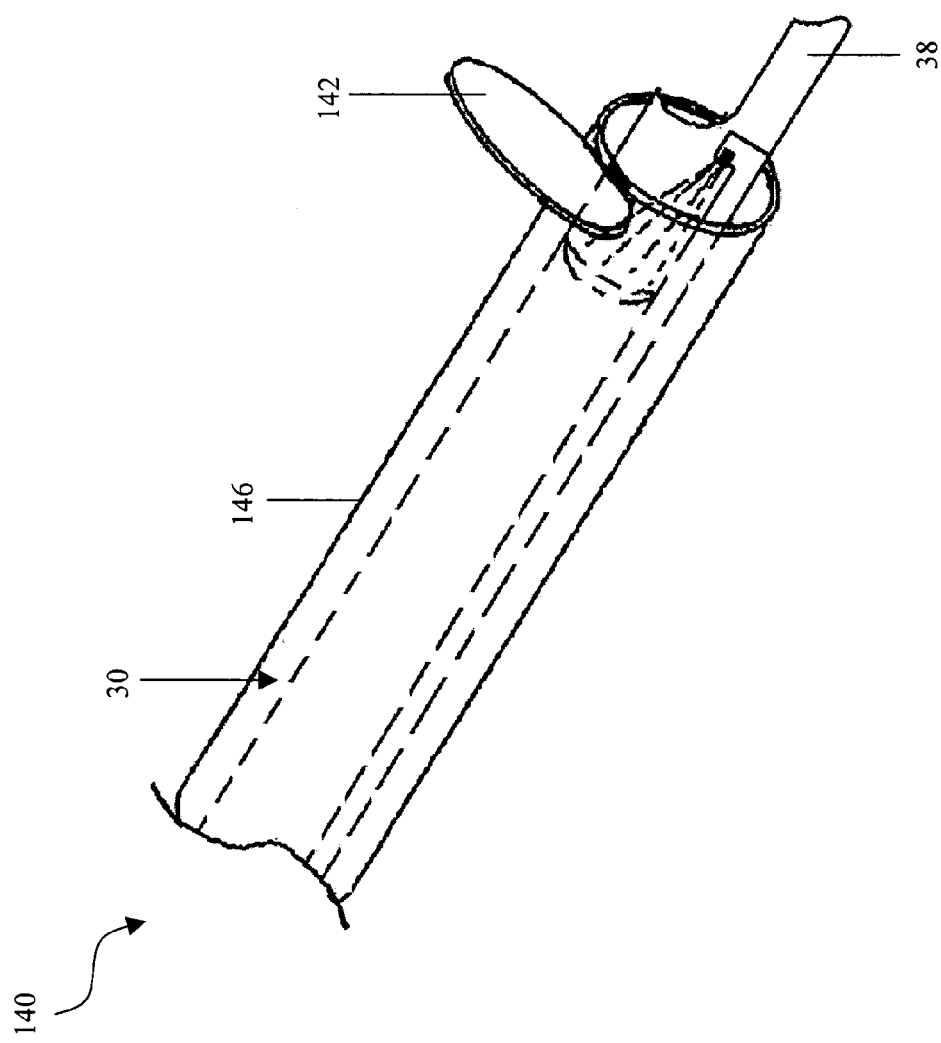
FIG. 6B is a perspective view of the tissue biopsy and processing device of FIG. 2 disposed within the isolation device of FIG. 6A.

In use, a tissue biopsy and processing device can be removably disposed within the shaft 146 of the isolation member 140, as shown in FIG. 6B. The biopsy and processing device is preferably slidably disposed within the isolation member 140 and movable between a first position, as shown, in which the hinged flap 142 is forced open and the biopsy member extends from the distal end of the shaft, and a second position, in which the hinged flap 142 is closed and the biopsy member is fully disposed within the shaft. Alternatively, the tissue biopsy and processing device can be integrally formed with the isolation member 140.

A person having ordinary skill in the art will appreciate that, while a hinged flap 142 is shown, a variety of isolation members can be used, including, for example, a rotatable door, a seal or gasket, or similar device. While virtually any isolation member can be used, the isolation member should be effective to enable a tissue sample to be retrieved, yet prevent fluid or other foreign substances from entering the reducing chamber after the tissue sample is retrieved.

The present invention also provides a method for preparing a tissue slurry using a tissue biopsy and processing device. In general, the method includes the steps of removing a tissue sample from a patient's body using the biopsy member, and processing the tissue sample with the processing element to dissociate and mince the tissue. The tissue can then be collected for subsequent use. The method is preferably performed in a sealed system in order to avoid any possible contamination of the tissue sample.

The features and other details of the invention will now be more particularly described and pointed out in the claims. It will be understood that the particular embodiments of the invention are shown by way of illustration and not as limitations of the invention. Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A tissue biopsy and processing device, comprising:
 a biopsy member adapted to remove a tissue sample from a patient;
 a processing apparatus having a tissue reducing chamber in communication with and adapted to receive the tissue sample from the biopsy member, and a tissue processing element associated with the tissue reducing chamber that is effective to dissociate the tissue sample retained within the tissue reducing chamber;
 a tissue retaining element located within the tissue reducing chamber for holding the tissue sample while the tissue processing element dissociates the tissue sample; and
 a bioimplantable tissue scaffold in communication with the processing apparatus and effective to receive the dissociated tissue sample from the tissue processing element.

2. The device of claim 1, wherein the device is in the form of an elongate member having a proximal end, a distal end, and an inner lumen extending therebetween, the biopsy member being formed on the distal end of the elongate member and the tissue reducing chamber being formed within the inner lumen proximal to the distal end of the elongate member.

3. The device of claim 2, wherein the biopsy member is effective to retrieve and convey a tissue sample to the tissue reducing chamber.

4. The device of claim 3, wherein the tissue processing element is disposed within the tissue reducing chamber.

5. The device of claim 1, wherein the biopsy member is selected from the group consisting a suction member, a cutting member, a burr, a shaver, a curette, a rongeur, a high pressure fluid jet, a grasping member, a needle, and combinations thereof.

6. The device of claim 1, wherein the tissue reducing chamber includes an isolation member effective to prevent foreign substances from entering the reducing chamber after a tissue sample is disposed within the chamber.

7. The device of claim 6, wherein the isolation member comprises a hinged flap movable between an open position, in which the chamber can receive a tissue sample, and a closed position, in which the chamber is sealed.

8. The device of claim 1, wherein the tissue processing element comprises a high pressure fluid jet.

9. The device of claim 1, wherein the tissue retaining element comprises a filter having pores sufficient to retain the tissue sample.

10. The device of claim 1, wherein the tissue processing element comprises a mechanical cutting element.

11. The device of claim 10, wherein the mechanical cutting element is selected from the group consisting of an auger, a rongeur, a curette, an awl, a reamer, a corer, a blade, a grinding member, a grating member, and combinations thereof.

12. The device of claim 1, wherein the tissue retaining element comprises a siphoning member in communication with the tissue reducing chamber that is effective to receive a tissue sample after the tissue sample is processed by the tissue processing element and to remove excess fluid from the tissue sample.

13. The device of claim 2, wherein the tissue processing element is slidably disposed within the tissue reducing chamber.

14. A method for preparing a tissue slurry, comprising:
providing a device having a biopsy member for retrieving a tissue sample from a patient, and a processing element disposed within a tissue reducing chamber in communication with the biopsy member and effective to dissociate and mince the tissue sample;
removing a tissue sample from a patient's body using the biopsy member, the tissue sample being collected in the tissue reducing chamber;
processing the tissue sample collected in the tissue reducing chamber with the processing element to dissociate and mince the tissue; and
collecting the dissociated and minced tissue on a biological implant located proximal to the tissue reducing chamber to prepare the biological implant for subsequent implantation.

15. The method of claim 14, wherein the biological implant comprises a tissue scaffold.

16. The method of claim 15, wherein the dissociated and minced tissue sample is disposed within a fluid, and wherein the tissue scaffold is fluid permeable to enable the fluid to flow therethrough, thereby separating the dissociated and minced tissue from the fluid.

17. The method of claim 14, wherein the particle size of the dissociated and minced tissue fragments is in the range of about 0.1 mm$^3$ to 3 mm$^3$.

18. The method of claim 14, wherein the particle size of the dissociated and minced tissue fragments is less than about 1 mm$^3$.

19. The method of claim 14, wherein the dissociated and minced tissue is in the form of an amorphous slurry.

* * * * *